(12) United States Patent
Koh et al.

(10) Patent No.: US 10,456,115 B2
(45) Date of Patent: Oct. 29, 2019

(54) ULTRASOUND SYSTEM AND CLUTTER FILTERING METHOD THEREOF

(71) Applicants: SAMSUNG ELECTRONICS CO., LTD., Suwon-si (KR); Industry-University Cooperation Foundation Sogang University, Seoul (KR)

(72) Inventors: Hyun-woo Koh, Yongin-si (KR); Yang-mo Yoo, Seoul (KR); Sun-mi Yeo, Seoul (KR); Woo-youl Lee, Seoul (KR); Young-tae Kim, Seongnam-si (KR); Hwan Shim, Seoul (KR); Hyung-joon Lim, Seoul (KR)

(73) Assignees: SAMSUNG ELECTRONICS CO., LTD., Suwon-si (KR); Industry-University Cooperation Foundation Sogang University, Seoul (KR)

( * ) Notice: Subject to any disclaimer, the term of this patent is extended or adjusted under 35 U.S.C. 154(b) by 1349 days.

(21) Appl. No.: 14/258,501

(22) Filed: Apr. 22, 2014

(65) Prior Publication Data
US 2014/0316274 A1 Oct. 23, 2014

Related U.S. Application Data

(60) Provisional application No. 61/814,507, filed on Apr. 22, 2013.

(30) Foreign Application Priority Data

Sep. 26, 2013 (KR) .................. 10-2013-0114319

(51) Int. Cl.
*A61B 8/08* (2006.01)
*G06T 7/10* (2017.01)
(Continued)

(52) U.S. Cl.
CPC .......... *A61B 8/5269* (2013.01); *A61B 5/1128* (2013.01); *A61B 8/06* (2013.01);
(Continued)

(58) Field of Classification Search
CPC ......... A61B 8/06; A61B 8/488; A61B 8/5269; A61B 5/1128; G01S 15/8977;
(Continued)

(56) References Cited

U.S. PATENT DOCUMENTS 8,306,293 B2 * 11/2012 Walker ................ G01S 7/52034
382/128
8,684,934 B2 * 4/2014 Kim .................... G01S 15/8981
367/155
(Continued)

FOREIGN PATENT DOCUMENTS

WO WO2018/099867 * 6/2018 ............... G01S 7/52

OTHER PUBLICATIONS

Ledoux et al. "Reduction of the Clutter Component in Doppler Ultrasound Signals Based on Singular Value Decomposition: A Simulation Study." Ultrasonic Medical Imaging 19, pp. 1-18 (1997).*
(Continued)

*Primary Examiner* — Amanda Lauritzen Moher
(74) *Attorney, Agent, or Firm* — Sughrue Mion, PLLC

(57) ABSTRACT

An ultrasound system and a clutter filtering method thereof are provided. The clutter filtering method includes: transmitting an ultrasound signal to an object; receiving a reflection signal reflected from the object; performing a singular value decomposition (SVD) on a plurality of doppler signals constituting the reflection signal; dividing a representation of the object into a plurality of regions according to a result of performing the SVD; determining cutoff frequencies of the plurality of regions according to different methods; and
(Continued)

performing clutter filtering on the plurality of regions by using the determined cutoff frequencies.

18 Claims, 8 Drawing Sheets

(51) Int. Cl.

| | | |
|---|---|---|
| *G06T 7/60* | (2017.01) | |
| *G06T 7/00* | (2017.01) | |
| *G06T 7/215* | (2017.01) | |
| *G06T 7/20* | (2017.01) | |
| *A61B 5/11* | (2006.01) | |
| *A61B 8/06* | (2006.01) | |
| *G01S 15/89* | (2006.01) | |
| *G06T 9/20* | (2006.01) | |

(52) U.S. Cl.
CPC .......... *A61B 8/488* (2013.01); *G01S 15/8977* (2013.01); *G01S 15/8981* (2013.01); *G06T 7/00* (2013.01); *G06T 7/0012* (2013.01); *G06T 7/10* (2017.01); *G06T 7/20* (2013.01); *G06T 7/215* (2017.01); *G06T 7/60* (2013.01); *G05B 2219/40326* (2013.01); *G06T 9/20* (2013.01); *G06T 2207/20112* (2013.01); *G06T 2207/20201* (2013.01)

(58) Field of Classification Search
CPC ..... G01S 15/8981; G06T 7/0012; G06T 7/20; G06T 7/215; G06T 7/10; G06T 7/60; G06T 7/00; G06T 9/20; G06T 2207/20201; G06T 2207/20112; G05B 2219/40326
See application file for complete search history.

(56) References Cited

U.S. PATENT DOCUMENTS

| | | | |
|---|---|---|---|
| 9,232,931 B2 * | 1/2016 | Kim ................. | G01S 15/8981 |
| 2003/0072470 A1 * | 4/2003 | Lee ................. | G06K 9/3241 |
| | | | 382/103 |
| 2005/0148875 A1 * | 7/2005 | Sato ................ | A61B 8/06 |
| | | | 600/453 |
| 2011/0118606 A1 * | 5/2011 | Kim ................. | G01S 15/8981 |
| | | | 600/453 |
| 2011/0275938 A1 * | 11/2011 | Kim ................. | A61B 8/06 |
| | | | 600/453 |
| 2013/0094729 A1 * | 4/2013 | Mauldin, Jr. ..... | G06K 9/6247 |
| | | | 382/128 |
| 2019/0029651 A1 * | 1/2019 | Patil ................ | A61B 8/0883 |
| 2019/0129026 A1 * | 5/2019 | Sumi ................ | G01S 13/90 |

OTHER PUBLICATIONS

Yoo et al. "Adaptive Clutter Rejection for 3D Color Doppler Imaging: Preliminary Clinical Study." Ultrasound in Medicine & Biology, pp. 1221-1231 (2008).*

Kargel et al. "Adaptive Clutter Rejection Filtering in Ultrasonic Strain-Flow Imaging." IEEE Trans Ultrason Ferroelectr Freq Control. 50(7), pp. 824-835 (2003).*

* cited by examiner

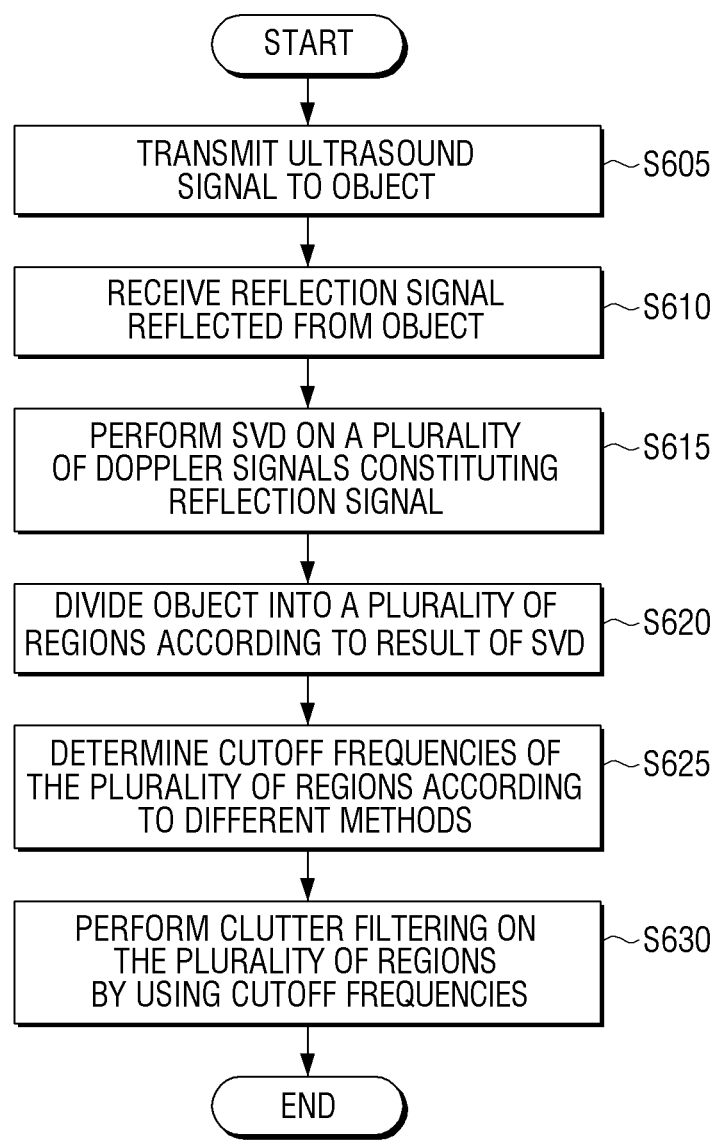

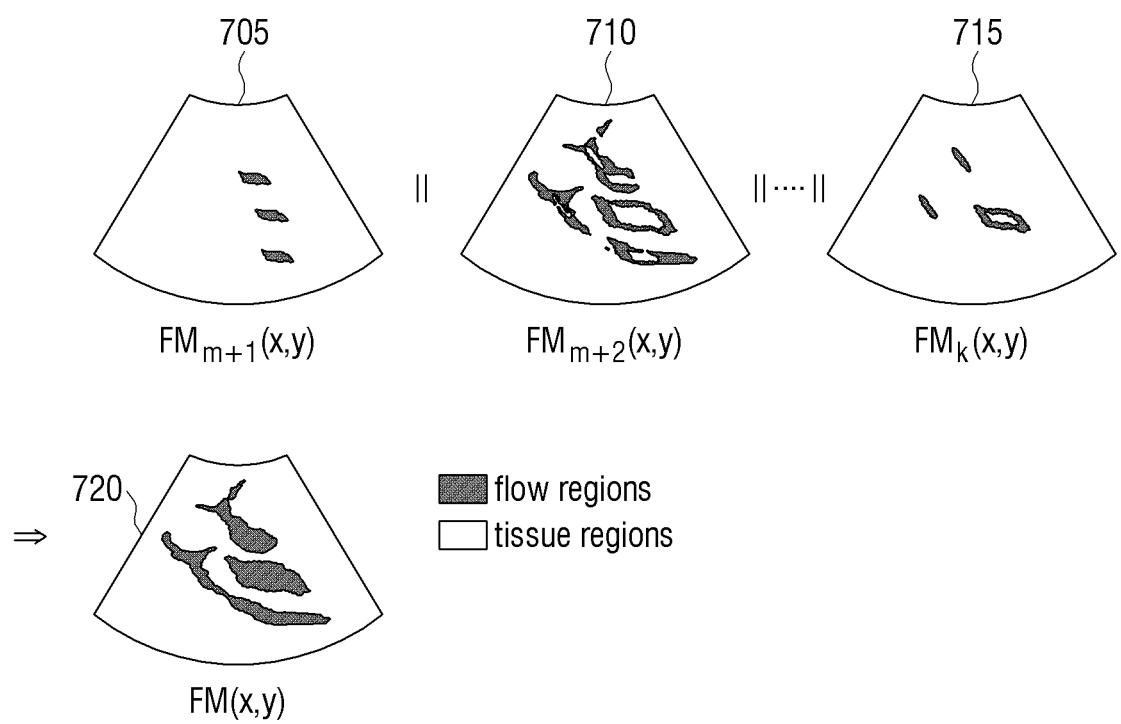

ULTRASOUND SYSTEM AND CLUTTER FILTERING METHOD THEREOF

CROSS-REFERENCE TO RELATED APPLICATION(S)

This application claims priority under 35 U.S.C. § 119 to Korean Patent Application No. 10-2013-0114319, filed on Sep. 26, 2013, in the Korean Intellectual Property Office, and U.S. Provisional Patent Application No. 61/814,507, filed on Apr. 22, 2013, in the United States Patent and Trademark Office, the disclosures of which are incorporated herein by reference in their entirety.

BACKGROUND

1. Field

The exemplary embodiments generally relate to an ultrasound system and a clutter filtering method thereof, and more particularly, to an ultrasound system that selects an optimized clutter eliminating filter, and a clutter filtering method thereof.

2. Description of the Related Art

An ultrasound system has noninvasive and nondestructive characteristics and thus has been widely used in the medical field to acquire information of internal organs of an object (in particular, a human body). The ultrasound system provides a doctor with an image of the internal organs of the object in real time without the need for a surgical operation to directly incise and observe the object. Therefore, the ultrasound system has important uses in the medical field.

The ultrasound system displays movements of a blood flow or tissues as a color Doppler image or a spectral Doppler image. A person inspecting such images, such as a doctor or the like, checks the color Doppler image or the spectral Doppler image to check various types of medical situations, such as a valve motion of the heart of the object, a blood flow rate or a blood flow amount of blood vessels of the object, etc.

The color Doppler image or the spectral Doppler image includes information about a velocity size and a velocity direction of the blood flow or the organs. Therefore, there is a need for methods of accurately measuring these types of information.

SUMMARY

Exemplary embodiments address at least the above problems and/or disadvantages and other disadvantages not described above. Also, the exemplary embodiments are not required to overcome the disadvantages described above, and an exemplary embodiment may not overcome any of the problems described above.

The exemplary embodiments provide an ultrasound system that selects an optimized filter to accurately acquire an ultrasound image, and a clutter filtering method thereof.

According to an aspect of an exemplary embodiment, there is provided a clutter filtering method of an ultrasound system, including: transmitting an ultrasound signal to an object; receiving a reflection signal reflected from the object; performing a singular value decomposition (SVD) on a plurality of doppler signals constituting the reflection signal; dividing a representation of the object into a plurality of regions according to a result of performing the SVD; determining cutoff frequencies of the plurality of regions according to different methods; and performing clutter filtering on the plurality of regions by using the determined cutoff frequencies.

The representation of the object may be divided into a tissue region and a flow region.

The determining of the cutoff frequencies of the plurality of regions according to the different methods may include: applying a tissue acceleration factor (TAF) method to the tissue region and applying the result of performing the SVD to the flow region to determine the cutoff frequencies of the tissue region and the flow region.

The performing of the SVD may include: forming a matrix defining a characteristic of the object by using the plurality of doppler signals; performing the SVD on the matrix to form a plurality of indexes for representing an ultrasound image of the object; and calculating an average frequency and a power of each of the plurality of indexes.

One of the plurality of regions, which has one of the plurality of indexes having an average frequency higher than a preset frequency and a power lower than a preset power, may be determined as the flow region, and the other regions among the plurality of regions may be determined as the tissue region.

The determining of the cutoff frequencies of the plurality of regions according to the different methods may further include: estimating a frequency of a doppler signal corresponding to the tissue region by using an autocorrelation method, multiplying the estimated frequency by a preset coefficient, and adding a result of the multiplying to the frequency to determine the cutoff frequency of the tissue region; and estimating a clutter signal from the flow region according to the result of performing the SVD and, if an average frequency of the estimated clutter signal is lower than or equal to a preset frequency, determining the average frequency as the cutoff frequency of the flow region.

According to another aspect of an exemplary embodiment, there is provided an ultrasound system including: an ultrasound transceiver configured to transmit an ultrasound signal to an object and receive a reflection signal reflected from the object; a controller configured to perform a singular value decomposition (SVD) on a plurality of doppler signals constituting the reflection signal, divide a representation of the object into a plurality of regions according to a result of performing the SVD, determine cutoff frequencies of the plurality of regions according to different methods, and perform clutter filtering on the plurality of regions by using the determined cutoff frequencies; and a display unit configured to display a signal on which the clutter filtering is performed, as an image.

When the controller divides the representation of the object into the plurality of regions, the controller may divide the representation of the object into a tissue region and a flow region.

When the controller determines the cutoff frequencies, the controller may apply a tissue acceleration factor (TAF) method to the tissue region and the result of performing the SVD to the flow region to determine the cutoff frequencies of the tissue region and the flow region.

When the controller performs the SVD, the controller may form a matrix defining a characteristic of the object by using the plurality of doppler signals, perform the SVD on the matrix to form a plurality of indexes for representing an ultrasound image of the object, and calculate an average frequency and a power of each of the plurality of indexes.

When the controller divides the representation of the object into the plurality of regions, the controller may determine one of the plurality of regions, which has one of the plurality of indexes having an average frequency higher than a preset frequency and a power lower than a preset power, as the flow region, and determine the other regions among the plurality of regions as the tissue region.

When the controller determines the cutoff frequencies of the plurality of regions according to the different methods, the controller may estimate a frequency of a doppler signal corresponding to the tissue region by using an autocorrelation method, multiply the estimated frequency and a preset coefficient to generate a multiplication result value, and add the multiplication result value to the frequency in order to determine the cutoff frequency of the tissue region, and may estimate a clutter signal from the flow region according to the result of performing the SVD and, if an average frequency of the estimated clutter signal is lower than or equal to a preset frequency, determine the average frequency as the cutoff frequency of the flow region.

BRIEF DESCRIPTION OF THE DRAWINGS

The above and/or other aspects will be more apparent by describing certain exemplary embodiments with reference to the accompanying drawings, in which:

FIG. 6 is a flowchart of a clutter filtering method according to an exemplary embodiment, and FIG. 7 illustrates flow masks according to an exemplary embodiment.

DETAILED DESCRIPTION OF THE EXEMPLARY EMBODIMENTS

Figure 1:
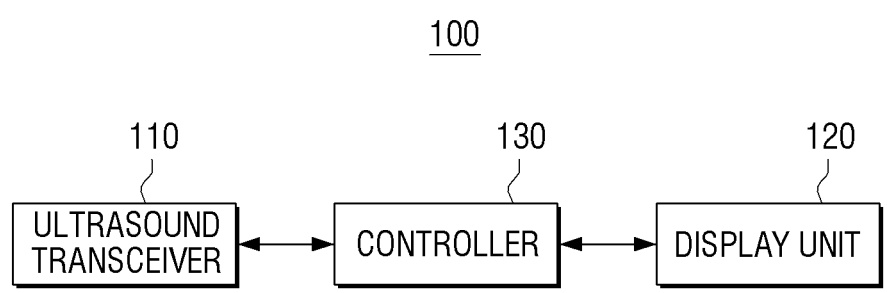
FIG. 1 is a block diagram illustrating a structure of an ultrasound system according to an exemplary embodiment.

Exemplary embodiments are described in greater detail with reference to the accompanying drawings.

In the following description, the same drawing reference numerals are used for the same elements even in different drawings. The matters defined in the description, such as a detailed construction and elements, are provided to assist in a comprehensive understanding of the exemplary embodiments. Thus, it is apparent that the exemplary embodiments can be carried out without those specifically defined matters. Also, well-known functions or constructions are not described in detail since they would obscure the exemplary embodiments with unnecessary detail.

FIG. 1 is a block diagram illustrating a structure of an ultrasound system 100 according to an exemplary embodiment. Referring to FIG. 1, the ultrasound system 100 includes an ultrasound transceiver 110, a display unit 120, and a controller 130. FIG. 1 exemplarily illustrates the ultrasound system 100 as an apparatus having elements configured to perform an ultrasound transceiving function, a display function, and a controlling function, as examples of essential elements. Therefore, according to exemplary embodiments, some of the elements of FIG. 1 may be omitted or changed, or other types of elements may be further added.

The ultrasound transceiver 110 transmits an ultrasound signal to an object and receives the ultrasound signal (e.g., an ultrasound echo signal) reflected from the object to acquire ultrasound data.

The ultrasound transceiver 110 may include a transmission signal former (not shown), an ultrasound probe (not shown) including a plurality of converter devices (not shown), a beam former (not shown), and an ultrasound data former (not shown).

The transmission signal former may form a transmission signal for acquiring an ultrasound image in consideration of positions and focusing points of the converter devices.

If the transmission signal is provided from the transmission signal former, the ultrasound probe may convert the transmission signal into the ultrasound signal, transmit the ultrasound signal to the object, and receive the ultrasound echo signal reflected from the object to form a reception signal. The reception signal is an analog signal. The ultrasound probe sequentially and repetitively transmits and receives ultrasound signals according to transmission signals sequentially provided from the transmission signal former, to form a plurality of reception signals. The ultrasound probe may include a three-dimensional (3D) mechanical probe, a two-dimensional (2D) array probe, etc.

If the reception signal is provided from the ultrasound probe, the beam former may perform an analog-to-digital conversion on the reception signal to form a digital signal. The beam former receives and focuses the digital signal in consideration of the positions and the focusing points of the converter devices to form a received and focused signal. The beam former may sequentially and repetitively perform an analog digital conversion, and receive and focus according to reception signals sequentially provided from the ultrasound probe, to form a plurality of received and focused signals.

If the received and focused signal is provided from the beam former, the ultrasound data former may form ultrasound data by using the received and focused signal. The ultrasound data former may sequentially and repetitively form ultrasound data according to the received and focused signals sequentially provided from the beam former to form a plurality of pieces of ultrasound data.

The display unit 120 displays a signal on which clutter filtering is performed, as an image. In other words, the display unit 120 may display an ultrasound image that is image-processed by the controller 130.

The controller 130 forms a plurality of ultrasound images by using the plurality of pieces of ultrasound data provided from the ultrasound transceiver 110 and estimates a degree of motion of the ultrasound probe to perform a motion correction image processing operation on the plurality of ultrasound images.

According to an exemplary embodiment, the controller 130 may perform a singular value decomposition (SVD) on a plurality of doppler signals constituting a reflection signal, divide the object (e.g., a representation of the object) into a plurality of regions according to the result of the SVD, determine cutoff frequencies of the plurality of regions according to different methods, and perform clutter filtering on the plurality of regions by using the determined cutoff frequencies.

Also, if the object is divided into the plurality of regions, the controller 130 may divide the object into a tissue region and a flow region. In other words, the controller 130 may perform the SVD on the plurality of doppler signals of the reflection signal received by the ultrasound transceiver 110 and divide the object into the tissue region and the flow region according to the result of the SVD. A detailed method of dividing the object into the tissue region and the flow region by the controller 130 will be described later.

If the cutoff frequencies are determined, the controller 130 may apply a tissue acceleration factor (TAF) method to the tissue region and the result of the SVD to the flow region in order to determine the cutoff frequencies of the tissue region and the flow region. According to an exemplary embodiment, the controller 130 may calculate a TAF value using any of several types of methods known to those skilled in the art, for the tissue region where there is no flow, to determine the cutoff frequency of the tissue region. Also, the controller 130 may use the result of the SVD for the flow region to determine the cutoff frequency of the flow region in consideration of an existence of the flow. A method of determining cutoff frequencies according to regions will be described later.

If the SVD is performed, the controller 130 may form a matrix defining a characteristic of the object by using the plurality of Doppler signals, perform the SVD on the matrix to form a plurality of indexes for representing the ultrasound image of the object, and respectively calculate average frequencies and powers of the plurality of indexes.

If the object is divided into the plurality of regions, the controller 130 may determine one of the plurality of regions, which has one of the plurality of indexes having an average frequency higher than a preset frequency and a power lower than a preset power value, as the flow region, and determine the other regions as the tissue region.

If the cutoff frequencies of the plurality of regions are determined according to different methods, the controller 130 may estimate a frequency of a doppler signal corresponding to the tissue region according to a correlation method, multiply the estimated frequency and a preset coefficient, and add the multiplication result value to the frequency to determine the cutoff frequency of the tissue region. Also, the controller 130 may estimate a clutter signal from the flow region according to the result of the SVD and, if an average frequency of the estimated clutter signal is lower than or equal to a preset frequency, determine the average frequency as the cutoff frequency of the flow region.

Therefore, a user may use the ultrasound system 100 as described above to divide the object into the flow region and the tissue region and select an optimized filter according to the flow region and the tissue region in order to effectively filter the clutter signal.

A method of dividing an object into a flow region and a tissue region to select an optimized filter will now be described in detail with reference to FIGS. 2 through 5.

Figure 2:
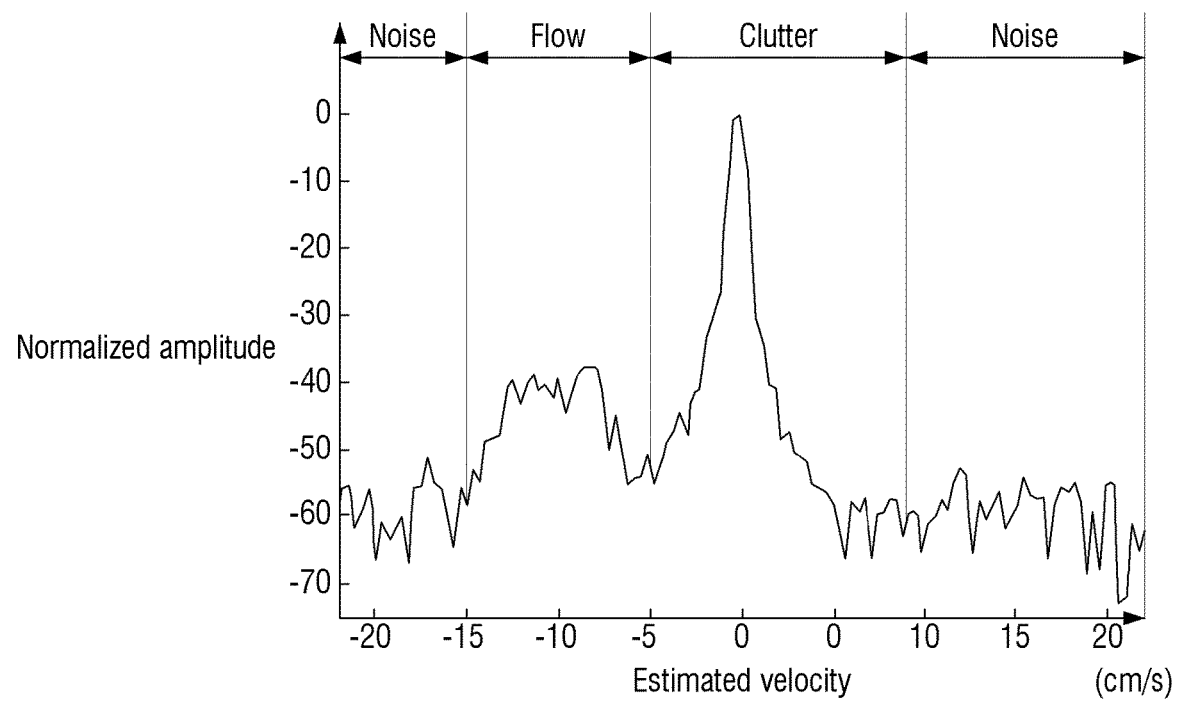
FIG. 2 is a graph illustrating a spectral analysis of a Doppler signal.

If the ultrasound transceiver 110 transmits an ultrasound signal to an object and receives a reflection signal reflected from the object, a frequency spectrum of a doppler signal in which cluster, flow, and noise signals are mixed may be acquired, as exemplarily shown in FIG. 2.

According to an exemplary embodiment, an amplitude of a clutter signal reflected from a blood vessel wall, heart muscles, or the like and an amplitude of a clutter signal reflected from a blood flow are very high, and thus it is not easy to estimate a frequency of only the doppler signal corresponding to the blood flow.

As shown in FIG. 2, an amplitude of a clutter signal section is higher than amplitudes of flow and noise signal sections. Thus, if the ultrasound system 100 is used to examine object (for example, a human body), an amplitude of a clutter signal, which is not necessary for an examination, may be much higher than a doppler signal of a blood flow necessary for the examination, thereby preventing an accurate examination. Therefore, there is a need for several methods of effectively eliminating the clutter signal.

Figure 3:
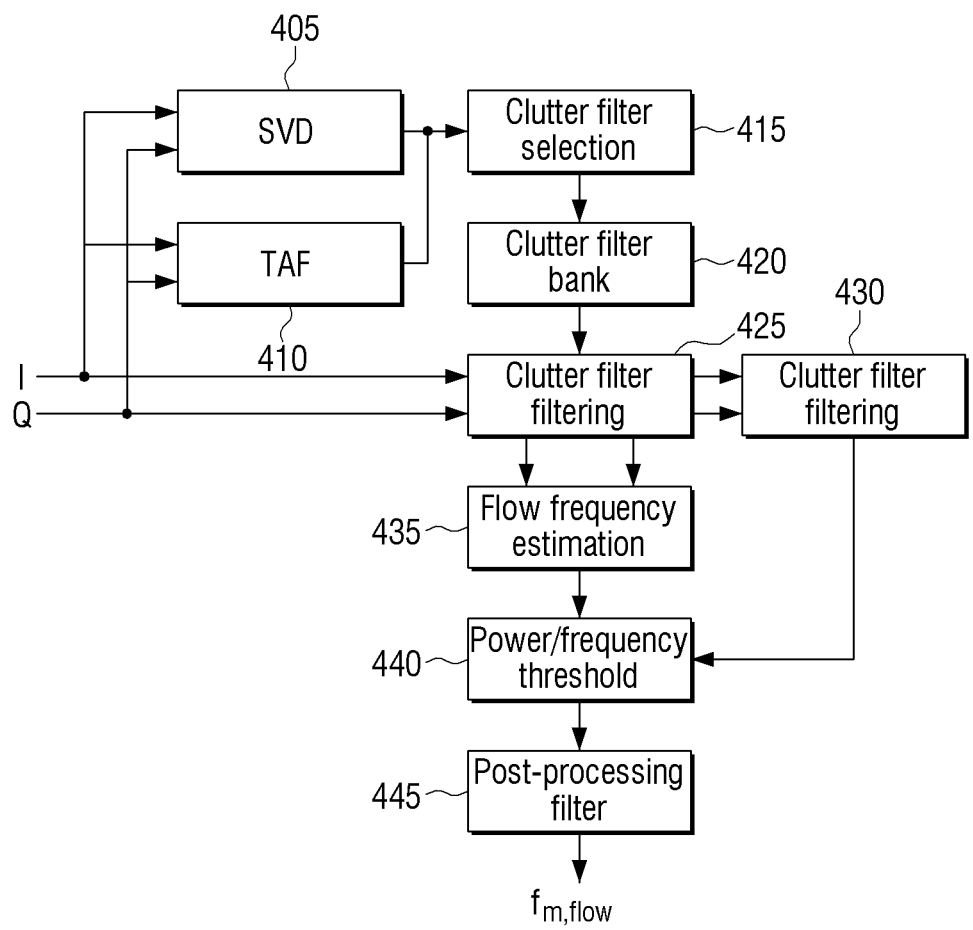
FIG. 3 is a block diagram illustrating a clutter filtering method according to an exemplary embodiment.

FIG. 3 is a block diagram illustrating a clutter filtering method according to an exemplary embodiment.

As shown in FIG. 3, the clutter filtering method may include operations of performing an SVD (operation 405) and a TAF (operation 410) on inphase and quadrature signals to search for characteristics of clutter signals varying in each image in order to select a clutter filter. The clutter filtering method may further include operations of performing clutter filter selection (operation 415), storing the selected filters in a clutter filter bank (operation 420), performing clutter filter filtering (operations 425 and 430), performing flow frequency estimation (operation 435), comparing the estimated flow frequency to a power/frequency threshold (operation 440), and performing post-processing filtering (operation 445).

According to an exemplary embodiment, the controller 130 may perform an SVD on a plurality of doppler signals constituting a reflection signal and divide an object into a plurality of regions according to the result of the SVD. In particular, the controller 130 may divide the object into a flow region where a flow exists and a tissue region where a flow does not exist.

The process of performing the SVD is known to those skilled in the art, and thus, a detailed description thereof is omitted.

Characteristics of clutter and flow signals that are scattered signals may be determined from a blood flow by using an m×n correlation matrix that is acquired from a backscattered doppler signal according to the result of performing the SVD.

Figure 4A:
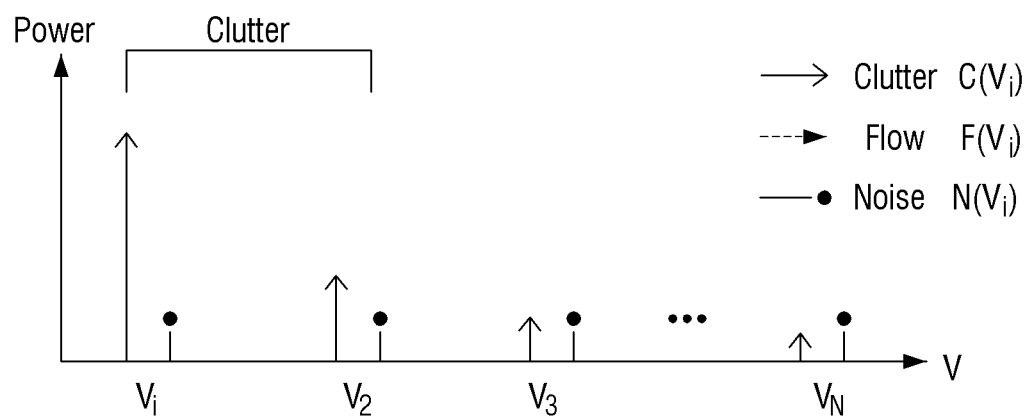
FIG. 4A is a graph illustrating a singular vector spectrum of a region where there is no flow.

As shown in FIG. 4A, the controller 130 may perform the SVD to acquire a spectrum that includes noise signals existing in all orders and a clutter signal having a high power and a low order in a region where a flow does not exist, e.g., in the tissue region.

Figure 4B:
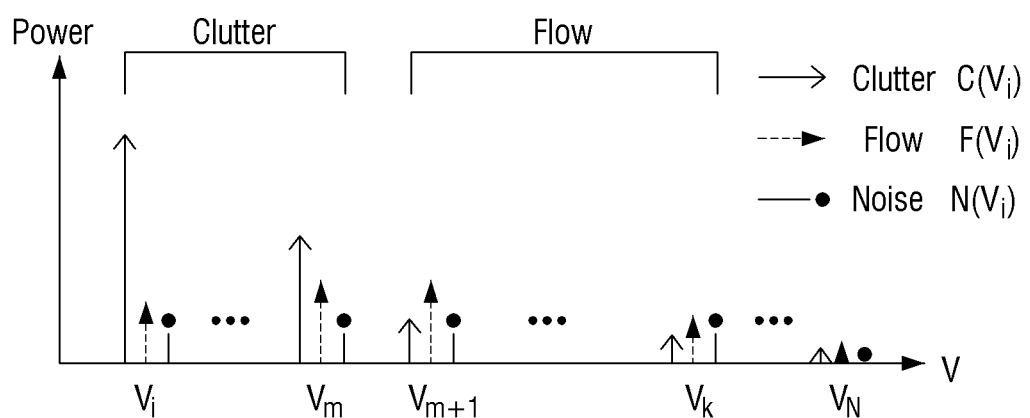
FIG. 4B is a graph illustrating a singular vector spectrum of a region where there is a flow.

Also, as shown in FIG. 4B, the controller 130 may perform the SVD to acquire a spectrum that includes a clutter signal having a high power and a low order and a flow signal having a power lower than the clutter signal and higher than a noise signal and having higher orders in the flow region.

In other words, the clutter signal has a higher power than the flow and noise signals and thus has lower orders V1 through Vm. Also, the flow signal has higher orders Vm+1 through Vk than the clutter signal.

A frequency and a power of a singular vector having an $i^{th}$ order may be acquired by Equations 1 and 2 below:

$$f_{svd}(i) = \frac{f_{PRF}}{2\pi}\tan^{-1}[R_{V_i\ V_i}(1)] \quad \text{Equation (1)}$$

$$P_{SVD}(i) = \Sigma(i, i) \quad \text{Equation (2)}$$

$f_{PRF}$ of Equation 1 denotes a pulse repetition frequency, and $R_{v_iv_i}(1)$ denotes a lag-one autocorrelation of a singular vector having an order of 1.

Also, a velocity may be acquired by using a frequency of Equation 1. A correlation between the frequency and the velocity may be determined using equations known to those skilled in the art, and thus, a detailed description thereof is omitted.

As described above, the controller 130 may divide an object into a flow region and a region where a flow does not exist, e.g., a tissue region, in order to select different clutter eliminating filters in the flow region and the tissue region.

In detail, the controller 130 may determine a cutoff frequency of the region where the flow does not exist, e.g., the tissue region, according to a TAF value and select a clutter eliminating filter according to the determined cutoff frequency.

According to an exemplary embodiment, a cutoff frequency higher than a cutoff frequency of a filter actually necessary to filter the flow signal is selected in the tissue region where the flow does not exist, or a region where clutter and flow signals overlap with each other is widened, thereby preventing the elimination of the flow signal through filtering. Therefore, the controller 130 may determine the cutoff frequency of the tissue region according to the TAF value.

A process of acquiring the TAF value is known to those skilled in the art, and thus, a detailed description thereof is omitted.

If a cutoff frequency of the flow region is determined by using a TAF value as shown in FIG. 4B, there may arise a problem of eliminating a flow signal through filtering. Therefore, the controller 130 may determine a cutoff frequency according to an SVD value used for dividing an object into regions.

In detail, the controller 130 may compare a frequency and a power value of an $i^{th}$ order in each of the image points acquired by Equations 1 and 2 with threshold values of a preset frequency and a preset power value, determine a region having values higher than the threshold values of the preset frequency and the preset power value as a tissue region, and determine a region having values lower than the thresholds as a flow region.

The controller 130 may acquire a final flow mask of the flow region by using Equation 5 below.

$$FM(x,y)=FM_{m+1}(x,y)//FM_{m+2}(x,y)// \ldots //FM_k(x,y) \qquad \text{Equation (5)}$$

The flow mask is an image that may be acquired by respectively setting a flow region pixel and a tissue region to 1 and 0. x and y of Equation 5 respectively denote coordinates of horizontal and vertical directions, and // denotes the OR operator of logical operators.

In other words, as shown in FIG. 7, the controller 130 may acquire flow masks of respective pixels of the flow region and sum the flow masks through the OR operator in order to acquire a final flow mask.

In detail, element 705 of FIG. 7 denotes an $m+1^{th}$-order flow mask, and element 710 of FIG. 7 denotes an $m+2^{th}$-order flow mask. The controller 130 may acquire a $k^{th}$-order flow mask 715 and acquire a final flow mask 720 through the OR operator.

The display unit 120 may display a doppler image as a 2-dimensional (2D) commercial film (CF) image. The 2D CF image is an image that may be displayed by displaying an average velocity, disturbances, and power information of a blood flow in all image points of a cross-sectional image as different colors according to directions and sizes of the image points of the blood flow. In other words, a brightness of the displayed image may denote the velocity of the blood flow, and the colors may denote directions.

A method of determining a cutoff frequency for selecting an optimized filter will now be described with reference to FIG. 5.

Figure 5:
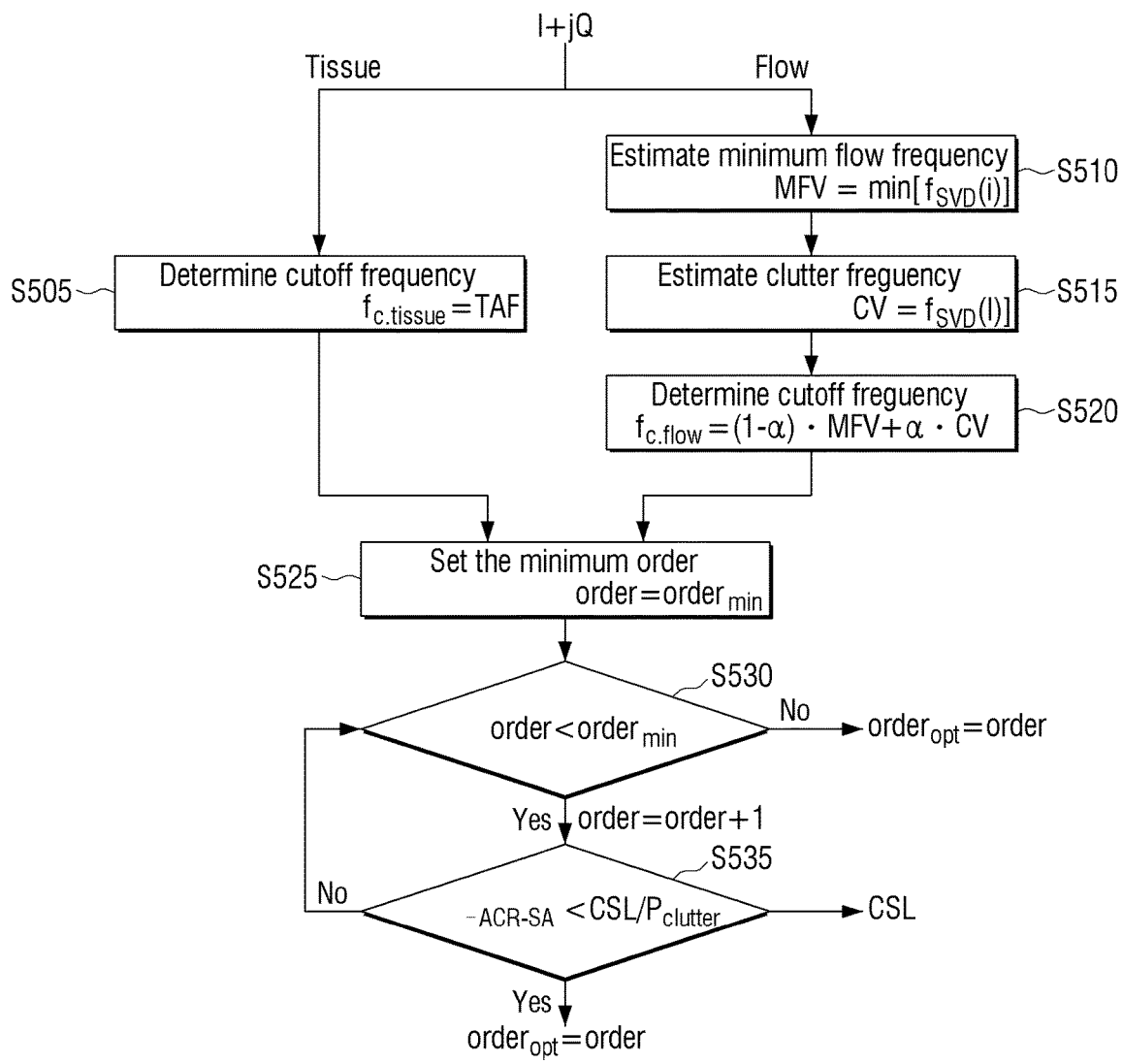
FIG. 5 is a flowchart of a method of determining a clutter filter according to an exemplary embodiment.

Referring to FIG. 5, in operation S505, a cutoff frequency of a tissue region is determined according to a TAF value.

In operation S510, a minimum flow frequency (MFV) of a flow region is estimated. In other words, the MFV may be a minimum value of $m+1^{th}$-order through $k^{th}$-order frequencies acquired according to a result of an SVD.

In operation S515, a first-order frequency value acquired according to the result of the SVD is estimated as a clutter frequency (CV). In other words, since power of a clutter signal is generally strong, the clutter signal may correspond to a singular vector having the lowest order. Therefore, the controller 130 estimates the first-order frequency value as the CV.

In operation S520, a cutoff frequency of the flow region is determined by using the MFV and the CV. In other words, the cutoff frequency of the flow region is determined by Equation 3.

$$f_{c,flow}=(1-\alpha)MFV+\alpha CV \qquad \text{Equation 3}$$

α of Equation 3 denotes a ratio between a clutter and a flow. In other words, a is a value that is used to determine a cutoff frequency between a clutter signal and a minimum flow velocity and may be experimentally determined.

If the cutoff frequencies of the tissue region and the flow region are determined, a minimum order is set in operation S525. In operation S530, a determination is made as to whether a current order is smaller than the minimum order. If it is determined in operation S530 that the current order is not smaller than the minimum order, the current order is determined as an optimized order.

If it is determined in operation S530 that the current order is smaller than the minimum order, the current order is increased by one order, and a clutter filter is determined by Equation 4 below in operation S535.

$$\vartheta_{AGR}(\text{order}, f_c) < \frac{CSL}{P_{clutter}} \qquad \text{Equation 4}$$

$f_c$ of Equation 4 denotes cutoff frequencies of the tissue and flow regions, CSL denotes a clutter suppression level, and $P_{clutter}$ denotes a clutter power.

In other words, if an optimized clutter filter for each frame is selected by using power of a clutter, changes of the power of the clutter caused by a cardiac cycle of the heart of a human body may be reflected.

FIG. 6 is a flowchart of a clutter filtering method according to an exemplary embodiment. Referring to FIG. 6, in operation S605, an ultrasound signal is transmitted to an object (for example, a human body). In operation S610, a reflection signal reflected from the object is received. In operation S615, an SVD is performed on a plurality of doppler signals constituting the reflection signal. In operation S620, the object is divided into a plurality of regions according to the result of the SVD. In other words, the object may be divided into a flow region where a flow exists and a region where a flow does not exist, e.g., a tissue region.

In operation S625, cutoff frequencies of the plurality of regions are determined according to different methods. In other words, the cutoff frequency of the flow region may be determined by using the result of the SVD, and the cutoff frequency of the tissue region may be determined by using a TAF value.

In operation S630, clutter filtering is performed on the plurality of regions by using the cutoff frequencies.

According to the above-described exemplary embodiments, a user may divide an object into flow and tissue regions to determine cutoff frequencies of the flow and tissue regions. Therefore, the user may select an optimized filter that may eliminate only a clutter signal from the flow region.

As described above, according to various exemplary embodiments, an ultrasound system may divide an object into flow and tissue regions to select an optimized filter, and a clutter filtering method may be performed by using the ultrasound system.

The clutter filtering method of the ultrasound system according to the above-described various exemplary embodiments may be coded as software and recorded on a non-transitory computer-readable medium installed in the ultrasound system. The controller 130 of the ultrasound system may execute the software recorded on the non-transitory computer-readable medium to perform clutter filtering.

In detail, the non-transitory computer-readable medium may store software that is configured to execute operations including: transmitting an ultrasound signal to an object; receiving a reflection signal reflected from the object; performing an SVD on a plurality of doppler signals constituting the reflection signal; dividing the object into a plurality of regions according to the result of the SVD; determining cutoff frequencies of the plurality of regions according to different methods; and performing clutter filtering on the plurality of regions by using the determined cutoff frequencies.

According to an exemplary embodiment, the term non-transitory computer-readable medium may refer to a medium which does not store data for a short time such as a register, a cache memory, a memory, or the like, but semi-permanently stores data and is readable by a device. For example, according to an exemplary embodiment, the above-described applications or programs may be stored and provided on a non-transitory computer readable medium such as a CD, a DVD, a hard disk, a blu-ray disk, a universal serial bus (USB), a memory card, a ROM, or the like.

The foregoing exemplary embodiments and advantages are merely exemplary and are not to be construed as limiting. The present teachings can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A clutter filtering method of an ultrasound system, comprising:
   transmitting an ultrasound signal to an object;
   receiving a reflection signal reflected from the object;
   performing a singular value decomposition (SVD) on a plurality of Doppler signals comprising the reflection signal;
   identifying a tissue region and a flow region of the object according to a result of performing the SVD;
   determining a cutoff frequency of the tissue region by estimating a frequency of the Doppler signal corresponding to the tissue region using an autocorrelation method, multiplying the estimated frequency by a preset coefficient, and adding a result of the multiplying to the estimated frequency and determining a cutoff frequency of the flow region by applying the result of performing the SVD to the flow region; and
   performing clutter filtering on the tissue region and the flow region by using the determined cutoff frequency of the tissue region and the flow region.

2. The clutter filtering method of claim 1, wherein the identifying the tissue region and the flow region comprises:
   dividing a representation of the object into the tissue region and the flow region.

3. The clutter filtering method of claim 2, wherein the determining the cutoff frequency of the tissue region and the flow region comprises:
   applying a tissue acceleration factor (TAF) method to the tissue region to determine the cutoff frequency of the tissue region.

4. The clutter filtering method of claim 3, wherein the performing the SVD comprises:
   forming a matrix defining a characteristic of the object by using the plurality of Doppler signals;
   performing the SVD on the matrix to form a plurality of indexes for representing an ultrasound image of the object; and
   calculating an average frequency and a power of each of the plurality of indexes.

5. The clutter filtering method of claim 4, wherein the identifying the tissue region and the flow region further comprises:
   determining one of a plurality of regions, which has one of the plurality of indexes having an average frequency higher than a preset frequency and a power lower than a preset power, as the flow region; and
   determining other regions among the plurality of regions as the tissue region.

6. The clutter filtering method of claim 5, wherein the determining the cutoff frequency of the tissue region and the flow region further comprises:
   estimating a clutter signal from the flow region according to the result of performing the SVD and, if an average frequency of the estimated clutter signal is lower than or equal to the preset frequency, determining the average frequency as a cutoff frequency of the flow region.

7. An ultrasound system comprising:
   an ultrasound transceiver configured to transmit an ultrasound signal to an object and receive a reflection signal reflected from the object;
   a controller configured to perform a singular value decomposition (SVD) on a plurality of Doppler signals comprising the reflection signal, identify a tissue region and a flow region of the object according to a result of performing the SVD, determine a cutoff frequency of the tissue region by estimating a frequency of the Doppler signal corresponding to the tissue region using an autocorrelation method, multiplying the estimated frequency by a preset coefficient, and adding a result of the multiplying to the estimated frequency and determine a cutoff frequency of the flow region by applying the result of performing the SVD to the flow region, and perform clutter filtering on the tissue region and the flow region by using the determined cutoff frequency of the tissue region and the flow region; and
   a display unit configured to display a signal on which the clutter filtering is performed, as an image.

8. The ultrasound system of claim 7, wherein when the controller divides a representation of the object into a plurality of regions, the controller divides the representation of the object into the tissue region and the flow region.

9. The ultrasound system of claim 8, wherein when the controller determines the cutoff frequency of the tissue region and the flow region, the controller applies a tissue acceleration factor (TAF) method to the tissue region to determine the cutoff frequency of the tissue region.

10. The ultrasound system of claim 9, wherein when the controller performs the SVD, the controller forms a matrix defining a characteristic of the object by using the plurality of Doppler signals, performs the SVD on the matrix to form a plurality of indexes for representing an ultrasound image of the object, and calculates an average frequency and a power of each of the plurality of indexes.

11. The ultrasound system of claim 10, wherein when the controller divides the representation of the object into the plurality of regions, the controller determines one of the plurality of regions, which has one of the plurality of indexes having an average frequency higher than a preset frequency and a power lower than a preset power, as the flow region, and determines other regions among the plurality of regions as the tissue region.

12. The ultrasound system of claim 11, wherein when the controller determines the cutoff frequency of the tissue region and the flow region of the plurality of regions according to the different methods, the controller estimates a clutter signal from the flow region according to the result of performing the SVD and, if an average frequency of the estimated clutter signal is lower than or equal to the preset frequency, determines the average frequency as a cutoff frequency of the flow region.

13. An ultrasound apparatus comprising:
an ultrasound transceiver configured to transmit an ultrasound signal to an object and receive a reflection signal reflected from the object;
a controller configured to identify, within the object, a flow region where flow exists and a tissue region where flow does not exist according to the reflection signal and a result of performing a singular value decomposition (SVD), select different clutter eliminating filters to eliminate clutter in the tissue region by estimating a frequency of a Doppler signal corresponding to the tissue region using an autocorrelation method, multiplying the estimated frequency by a preset coefficient, and adding a result of the multiplying to the estimated frequency, and in the flow region by applying the result of performing the singular value decomposition (SVD) to the flow region, and perform clutter filtering on a signal comprising the flow region and the tissue region using the selected clutter eliminating filters to output a clutter filtered signal; and
a display configured to display the clutter filtered signal as an image.

14. The ultrasound apparatus of claim 13, wherein the controller is configured to select the different clutter eliminating filters based on a cutoff frequency of the flow region and the tissue region.

15. The ultrasound apparatus of claim 14, wherein the controller is configured to use a first method to determine the cutoff frequency of the flow region and a second method different from the first method to determine the cutoff frequency of the tissue region.

16. The ultrasound apparatus of claim 15, wherein the reflection signal comprises a plurality of Doppler signals, and the controller is configured to perform a singular value decomposition (SVD) on the plurality of Doppler signals and divide a representation of the object into the flow region and the tissue region according to a result of the SVD.

17. The ultrasound apparatus of claim 16, wherein the controller is configured to determine a signal having a highest power among a plurality of signals as a clutter signal, and determine signals having lower powers than the clutter signal as flow and noise signals.

18. The ultrasound apparatus of claim 13, wherein the display is configured to display the image as a 2-dimensional (2D) commercial film (CF) image.

* * * * *